(12) United States Patent
Regnier et al.

(10) Patent No.: US 6,170,981 B1
(45) Date of Patent: Jan. 9, 2001

(54) IN SITU MICROMACHINED MIXER FOR MICROFLUIDIC ANALYTICAL SYSTEMS

(75) Inventors: Fred Regnier, West Lafayette, IN (US); Bing He, Newbury Park, CA (US)

(73) Assignee: Purdue Research Foundation, West Lafayette, IN (US)

(*) Notice: Under 35 U.S.C. 154(b), the term of this patent shall be extended for 0 days.

(21) Appl. No.: 09/306,547

(22) Filed: May 6, 1999

Related U.S. Application Data (60) Provisional application No. 60/084,528, filed on May 6, 1998.

(51) Int. Cl.$^7$ ...................................................... B01F 5/06
(52) U.S. Cl. ............................................................ 366/336
(58) Field of Search ............................ 366/181.5, 181.6, 366/336, 337, 340; 48/189.4; 138/37, 39

(56) References Cited

U.S. PATENT DOCUMENTS

| | | | | |
|---|---|---|---|---|
| 1,637,697 | * | 8/1927 | Jacobsen | 366/336 |
| 3,998,597 | * | 12/1976 | Forrest | 366/181.5 |
| 4,027,857 | * | 6/1977 | Cunningham | 366/340 |
| 4,594,005 | * | 6/1986 | Sakamoto et al. | 366/181.5 |

FOREIGN PATENT DOCUMENTS

600937 * 6/1978 (CH) ..................................... 366/340

* cited by examiner

Primary Examiner—Charles E. Cooley
(74) Attorney, Agent, or Firm—Woodard, Emhardt, Naughton, Moriarty & McNett (57) ABSTRACT

The present invention relates to an in situ micromachined mixer for microfluidic analytical systems. In a preferred embodiment, a 100 pL mixer for liquids transported by electroosmotic flow (EOF) is described. Mixing was achieved in multiple intersecting channels with a bimodal width distribution and varying lengths. Five $\mu$m width channels ran parallel to the direction of flow whereas larger 27 $\mu$m width channels ran back and forth through the network at a 45° angle. All channels were approximately 10 $\mu$m deep. It was observed that little mixing of confluent streams occurred in the 100 $\mu$m wide mixer inlet channel where mixing would be achieved almost exclusively by diffusion. In contrast, mixing was complete after passage through the channel network in the ≈200 $\mu$m length mixer. Solvent composition was altered by varying the voltage on solvent reservoirs. The high efficiency attained in this mixer was attributed to the presence of a 2 pL vortex in the center of the mixer. Video tracking of fluorescent particles with a fluorescence microscope allowed the position and volume of this vortex to be determined.

6 Claims, 7 Drawing Sheets

IN SITU MICROMACHINED MIXER FOR MICROFLUIDIC ANALYTICAL SYSTEMS

The present application claims priority from United States Provisional Patent Application Serial No. 60/084,528, filed May 6, 1998.

STATEMENT OF GOVERNMENT RIGHTS

This invention was made with U.S. Government support from the National Institutes of Health under Grant Number 25431. The U.S. Government has certain rights in this invention.

TECHNICAL FIELD OF THE INVENTION

The present invention generally relates to the mixing of confluent liquid streams in microfluidic systems and, more particularly, to an in situ micromachined mixer for microfluidic analytical systems.

BACKGROUND OF THE INVENTION

Merging two or more liquids to form a solution generally requires some combination of convective and diffusive transport. This is a critical element of many analytical methods. Although blending by convective transport alone can be achieved very quickly, it only provides a macroscopic level of mixing. Efficient mixing within convectively generated microenvironments requires diffusion. Diffusive mixing is most effective when the transport distance is a few microns or less.

Convective transport is a physical process requiring energy. Generally, this energy is provided in the form of mechanical agitation, as in the case of mechanical stirrers or vortex mixers. This direct addition of energy at the point of mixing is perhaps the reason this form of mixing is referred to as "dynamic mixing." Liquids may also be mixed by transport through a bed of particles where eddy diffusion and laminar flow provide the convective mixing element. An external pump or gravity drives convection in this case. This form of mixing is often referred to as "static mixing," possibly because there is no mechanical component at the point of mixing. Actually, any system in which there is convective transport is in a dynamic state of flux. The term static mixing is obviously both a misnomer and a contradiction but will be used herein because of its broad usage in the literature.

Mixing confluent liquid streams is an important, but difficult operation in microfluidic systems. Electroosmotically driven, microfluidic analytical systems in which mixing occurs in channels of 50–100 $\mu$m width are known in the art. Such mixing is generally achieved by laterally merging liquid streams in the same plane into a central channel at a T, Y, or + junction, where they mix by lateral diffusion. Channels of this width are too large for rapid diffusive mixing and too small to allow installation of a dynamic mechanical mixer. Some type of static mixer capable of substantial lateral transport would seem to be a better alternative. Because the volume of current microfluidic systems is generally in the range of 1–10 nL/cm and it would be desirable to achieve mixing within 0.1–1 mm of transport distance along a channel, mixing would have to be achieved in a volume of 0.1–2 nL. The question is how to build a static mixer of this volume with a high degree of lateral transport.

Designing a static mixer to solve this problem is facilitated by an analysis of mixing in particle beds. Longitudinal mixing along the flow axis through the bed results from i) laminar flow in the interparticle space, ii) poor mass transfer between stagnant pools of liquid within the particle matrix, and iii) radial differences in the rate of analyte transport. Even higher degrees of mixing can be achieved by using porous particles to increase the volume of stagnant mobile phase and limit mass transfuser further. Because this is a kinetic process, the degree of longitudinal mixing is flow rate dependent. Obviously, longitudinal mixing is most important when there is a longitudinal, or time based variation in the composition of the liquid stream entering the mixer. This is not the case in the microfluidic systems described above. The problem is a spatial difference produced by two, or more streams entering the mixer at different points. This is almost totally an issue of lateral heterogeneity. Lateral mixing is achieved in packed beds by transchannel mixing. As liquid from adjacent streams merges between particles there is both diffusive mixing and some degree of flow heterogeneity arising from packing variations within the bed. Transchannel coupling is very effective in averaging small degrees of lateral heterogeneity within chromatography columns, but does so over the length of many particles and a relatively large volume. The degree of lateral mixing in packed beds is too small to accommodate the substantial lateral heterogeneity encountered in merging two streams in microfluidic systems.

There is therefore a need for a static mixer i) of less than 500 pL total volume, ii) capable of continuously mixing two streams of liquid, and iii) having a high degree of lateral mixing. The present invention is directed toward meeting this need.

SUMMARY OF THE INVENTION

The present invention relates to an in situ micromachined mixer for microfluidic analytical systems. In a preferred embodiment, a 100 pL mixer for liquids transported by electroosmotic flow (EOF) is described. Mixing was achieved in multiple intersecting channels with a bimodal width distribution and varying lengths. Five $\mu$m width channels ran parallel to the direction of flow whereas larger 27 $\mu$m width channels ran back and forth through the network at a 45° angle. All channels were approximately 10 $\mu$m deep. It was observed that little mixing of confluent streams occurred in the 100 $\mu$m wide mixer inlet channel where mixing would be achieved almost exclusively by diffusion. In contrast, mixing was complete after passage through the channel network in the ≈200 $\mu$m length mixer. Solvent composition was altered by varying the voltage on solvent reservoirs. The high efficiency attained in this mixer was attributed to the presence of a 2 pL vortex in the center of the mixer. Video tracking of fluorescent particles with a fluorescence microscope allowed the position and volume of this vortex to be determined.

In one form of the present invention a microfluidic mixer is disclosed, comprising an inlet; an outlet, wherein the inlet and the outlet define a flow axis; a first flow channel extending between the inlet and the outlet, the first flow channel comprising a plurality of channel segments coupled for fluid flow therebetween, wherein each of the channel segments is oriented at a respective non-zero angle to the flow axis; and at least one second flow channel, each of said at least one second flow channels allowing fluid flow between two of the channel segments substantially parallel to the flow axis.

In another form of the present invention a microfluidic mixer is disclosed, comprising an inlet; an outlet, wherein the inlet and the outlet define a flow axis; a first flow channel extending between the inlet and the outlet, the first flow channel comprising a plurality of channel segments coupled for fluid flow therebetween, wherein one half of the channel segments are oriented at an acute angle to the flow axis and another half of the channel segments are oriented at an obtuse angle to the flow axis; and a plurality of second flow channels, each of the plurality of second flow channels allowing fluid flow between an acute angled channel segment and an obtuse angled channel segment.

DETAILED DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Transport channels in microfluidic systems are most frequently formed by wet etching roughly 10–20 $\mu$m deep channels of 100 $\mu$m width into an inorganic substrate and enclosing them with a transparent plate. Polysilicon, glass, and quartz are the materials of choice in microfabricated, microfluidic systems because of their wide use in electronics and micro-electromechanical systems and because of the advancement of the technology for micromachining silicons and silicates, which has accumulated substantially during the past three decades. Because polysilicon is a semiconductor, its use in electroosmotically driven systems is restricted without further surface modification. This is not an issue in pressure driven mixing. Recently, channels have been molded and cast into polymers in an effort to reduce fabrication cost; but the spectral properties of organic polymers can limit detection. Quartz was chosen for the preferred embodiment mixer of the present invention based on i) the desire to electroosmotically drive liquid through the mixer in some cases, ii) its outstanding heat transfer characteristics, iii) the case with which high resolution fabrication can be achieved in quartz, and iv) the fact that it is optically transparent across the ultraviolet and visible spectrum and would allow direct spectral observation of mixing. This latter property is also important when the mixer is integrated into an analytical system using absorbency or fluorescence detection.

As noted hereinabove, continuous mixing in prior art microchannel systems is generally achieved by horizontally merging streams of liquid in a single channel at a junction in a planar system of channels. When liquid transport is driven exclusively by electroosmotic flow (EOF) there is little, if any, laminar flow in the channels and the requisite lateral mixing must be achieved by diffusion. Diffusion alone does not provide rapid mixing of confluent streams in channels of >50 $\mu$m width when liquid transport is driven by EOF. Laminar flow in driven systems would obviously provide a higher degree of mixing, but would probably still not have sufficient lateral mixing.

It is known that heterogeneity in packing density and particle size increase both lateral and longitudinal mixing in pressure driven systems by providing a range of channel sizes. But it is not possible to organize or direct heterogeneity to specific regions of the bed because the positioning of large particles and voids cannot be controlled. In contrast, the preferred embodiment of the present invention utilizes microfabricated systems which mimic particle beds and allow structures and channels of specified shape and size (to a micron) to be placed at any position in the bed. This means that channel heterogeneity may be precisely controlled. A preferred embodiment micromachined mixer of the present invention is illustrated in a photomicrograph in FIG. 1A and as a plan view drawing in FIG. 1B, and is indicated generally at 10. The mixer 10 utilizes a bimodal distribution of channel dimensions, with relatively small 5 $\mu$m wide channels 12 oriented parallel to the flow axis and varying in length, as well as relatively large 27 $\mu$m wide channels 14 weaving across the bed at 45° and 135° angles to the flow axis. The logic behind this design is that the bulk of the fluid flow will travel through the larger channels 14 and move laterally, back and forth, across the system 10 during transport through the bed. A smaller volume of liquid will enter the minor 5 $\mu$m width channels 12 and travel longitudinally through the system 10. This mixer 10 is roughly 200 $\mu$m in length and has a volume of approximately 100 pL. Liquids could be introduced into the system 10 at two points; A or B. Solutions exit through a sonically drilled outlet in the cover plate (not shown).

Figure 1A:
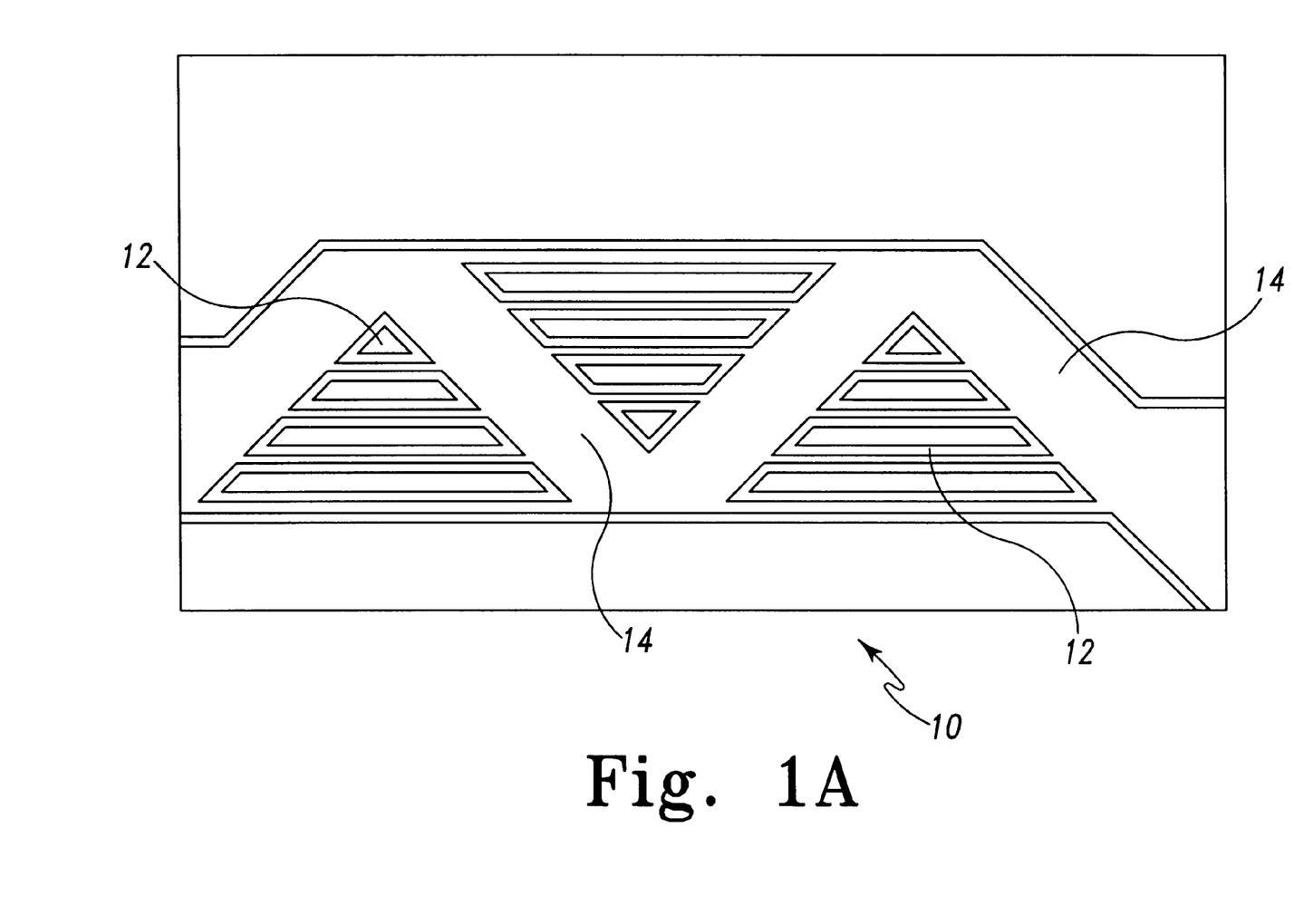
FIG. 1A is a digitized copy of a photomicrograph of a preferred embodiment in situ micromachined, multi-channel microfluidic mixer of the present invention.
Figure 1B:
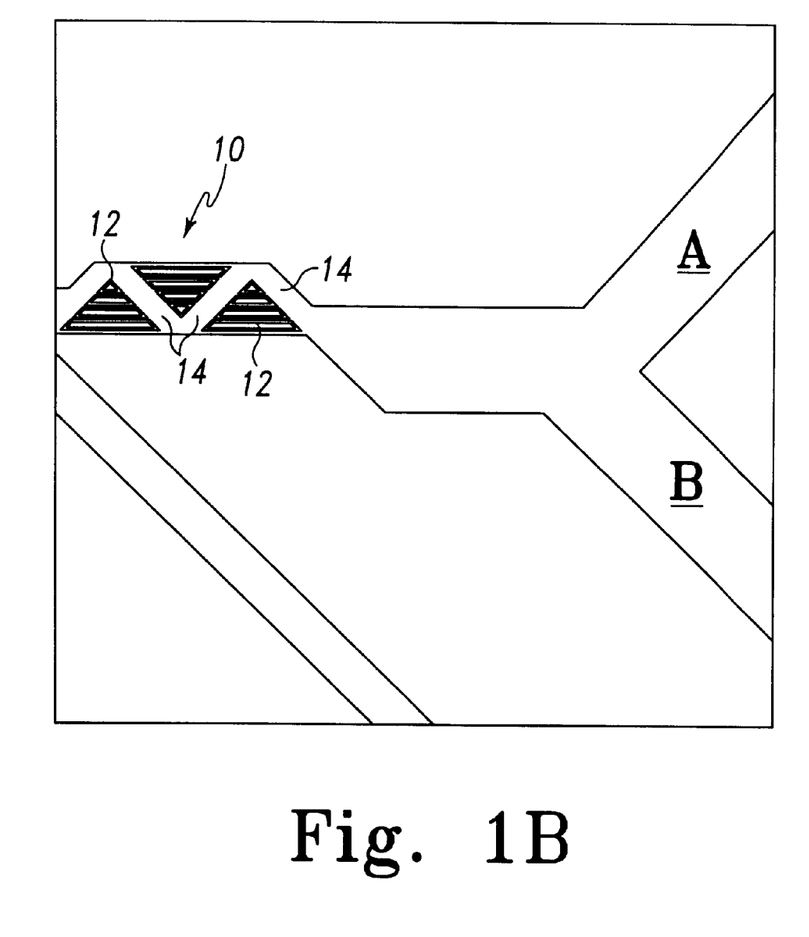
FIG. 1B is a plan view drawing of the mixer of FIG. 1A.

It is desirable in the construction of the mixer 10 in FIG. 1 to assure that channel width may be controlled to the micron level during fabrication. Forming 10 $\mu$m deep channels of $\leq$10 $\mu$m width is preferably achieved with microlithography and anisotropic gas phase etching. Anisotropic etching is directed vertically into the surface of the wafer where aspect ratios of 30/1 or greater are achieved. This is much more difficult with the isotropic wet etching procedures normally used in the construction of microfluidic systems. Channel depth, i.e. depth of the mixer 10 bed, generally ranged from 8–10 $\mu$m in the preferred embodiment quartz wafers. It was found to be difficult to etch deeper in quartz with current reactive ion etching technology. Deeper beds could probably be constructed by etching mirror image mixers on two wafers and bonding them on top of each other in such a away as to form a single mixer.

Figure 2A:
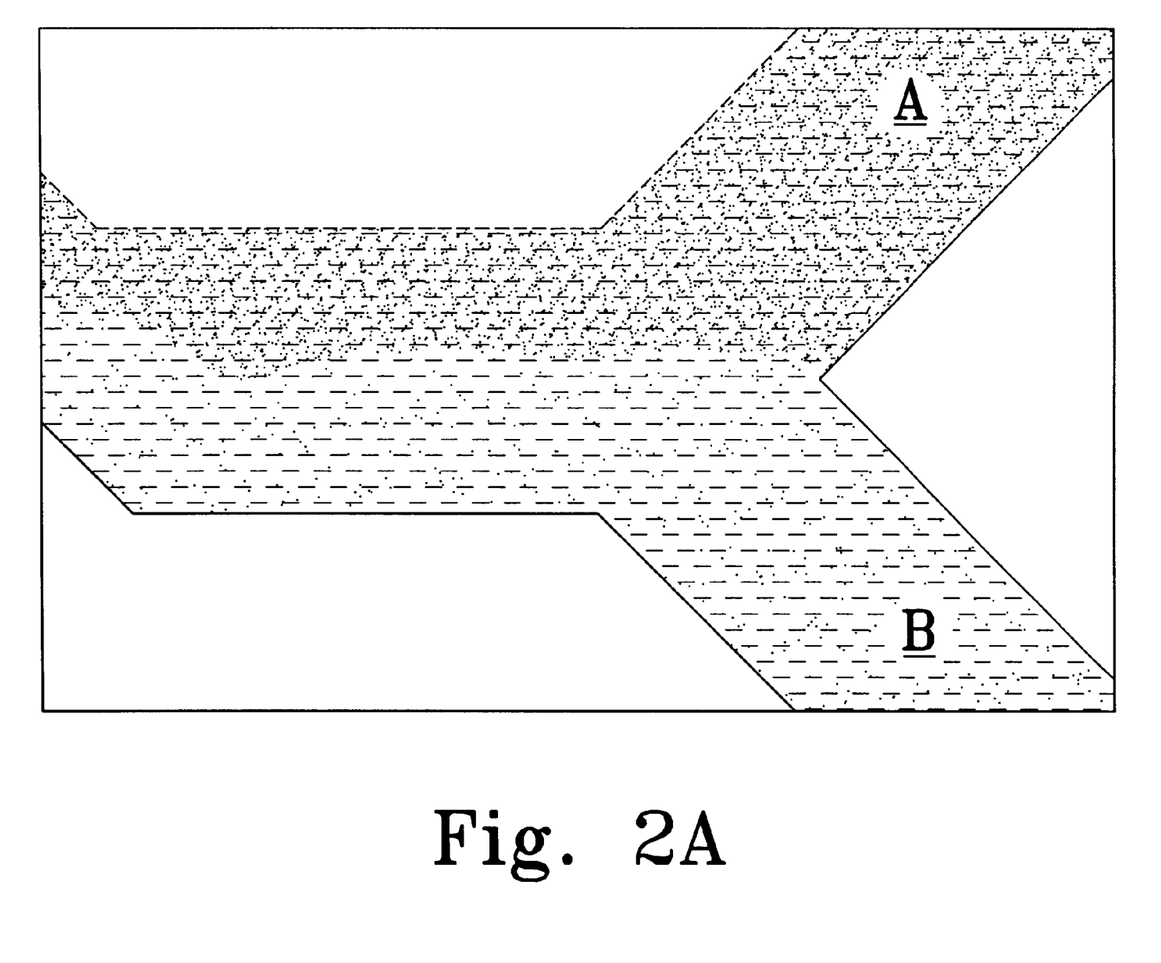
FIGS. 2A–B are digitized copies of photomicrographs of mixing in the microfluidic mixer of FIG. 1 at the mixer inlet and at the mixer outlet, respectively.
Figure 2B:
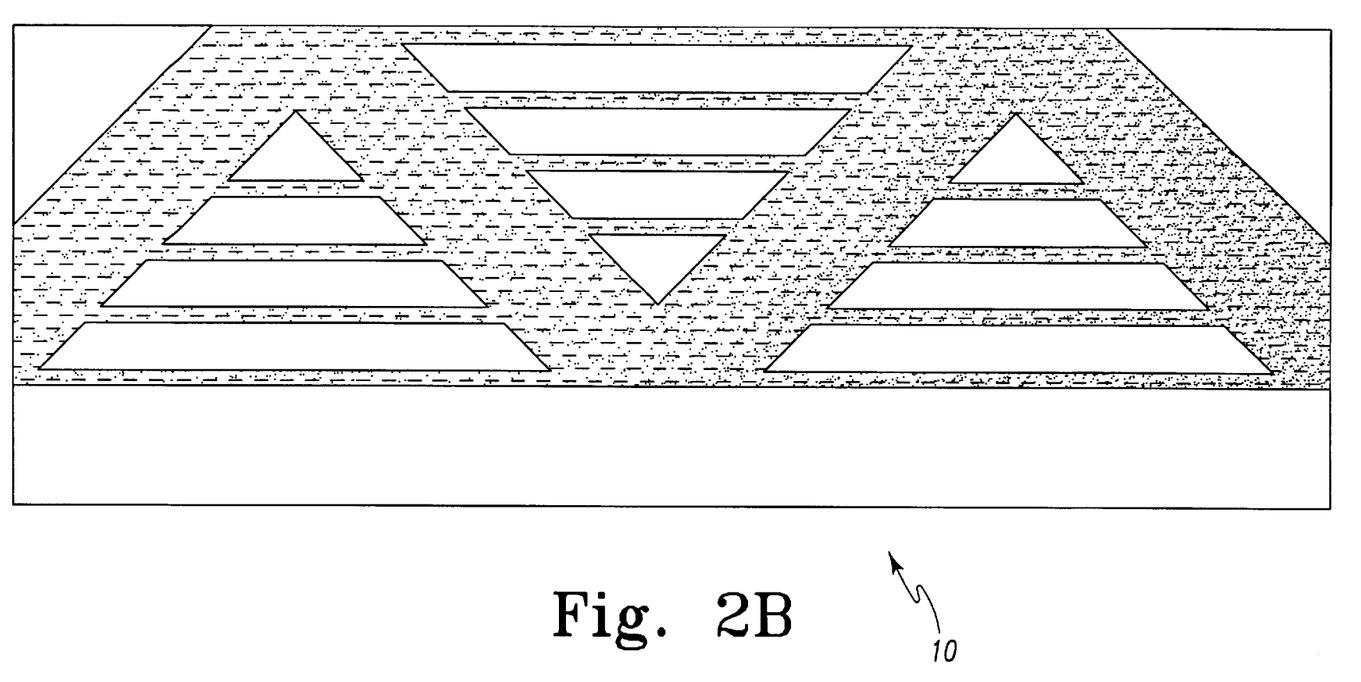

Electroosmotically driven flow was used to obtain the results described herein. Using 0.2 $\mu$m fluorescence labeled particles and a microscope with a provision for the observation and video taping of fluorescence, it was possible to examine mixing at the level of $\geq$1 $\mu$m. When buffer stream A was merged with a similar, fluorescent particle bearing stream B in the 50 $\mu$m wide inlet of the mixer 10, there was little mixing within the initial 100 $\mu$m transport distance (FIG. 2A). Similar observations have been reported in prior art cross-type mixers. In contrast, mixing after passage through the 200 μm long mixer 10 appears visually to be complete (FIG. 2B).

Figure 3:
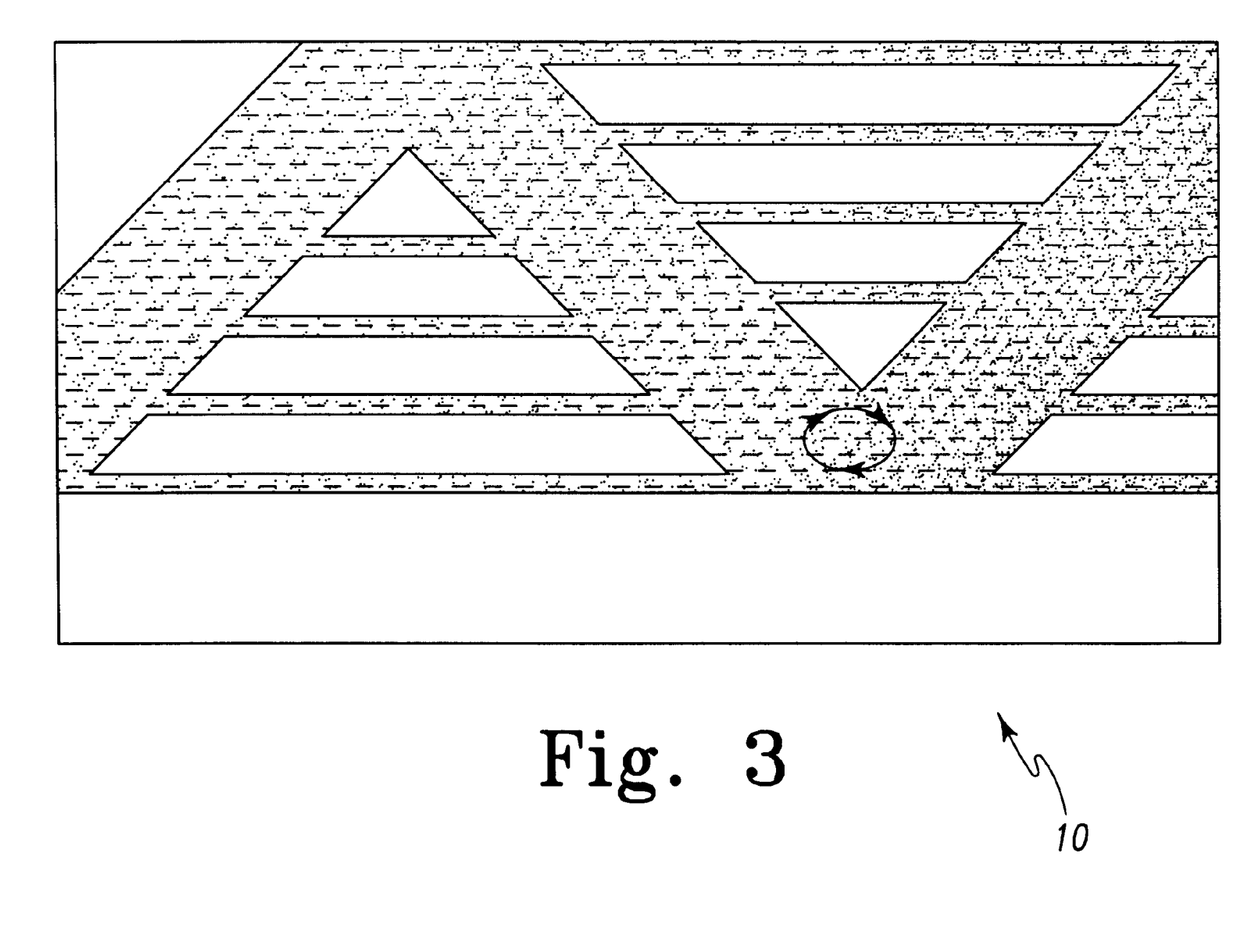
FIG. 3 is a digitized copy of a photomicrograph showing the position of a vortex in the mixer of FIG. 1, indicated by the path of trapped fluorescent particles.

During the course of microscopically evaluating the mixer 10, it was noted that micron size fluorescent particles were occasionally swept into the mixer 10 and retained in a vortex of counter clockwise rotation, as shown in FIG. 3. The position and shape of the vortex indicated in FIG. 3 were determined by observing the path of a fluorescent particle on successive frames of a video recording of the operating mixer 10. One video recording showed a particle cycling in this vortex for a minute before being expelled. The mechanism by which the vortex and perhaps counter flow is generated in the mixer 10 still remains to be determined. It should also be noted that vortices were never observed at other positions in the mixer 10.

Figure 4:
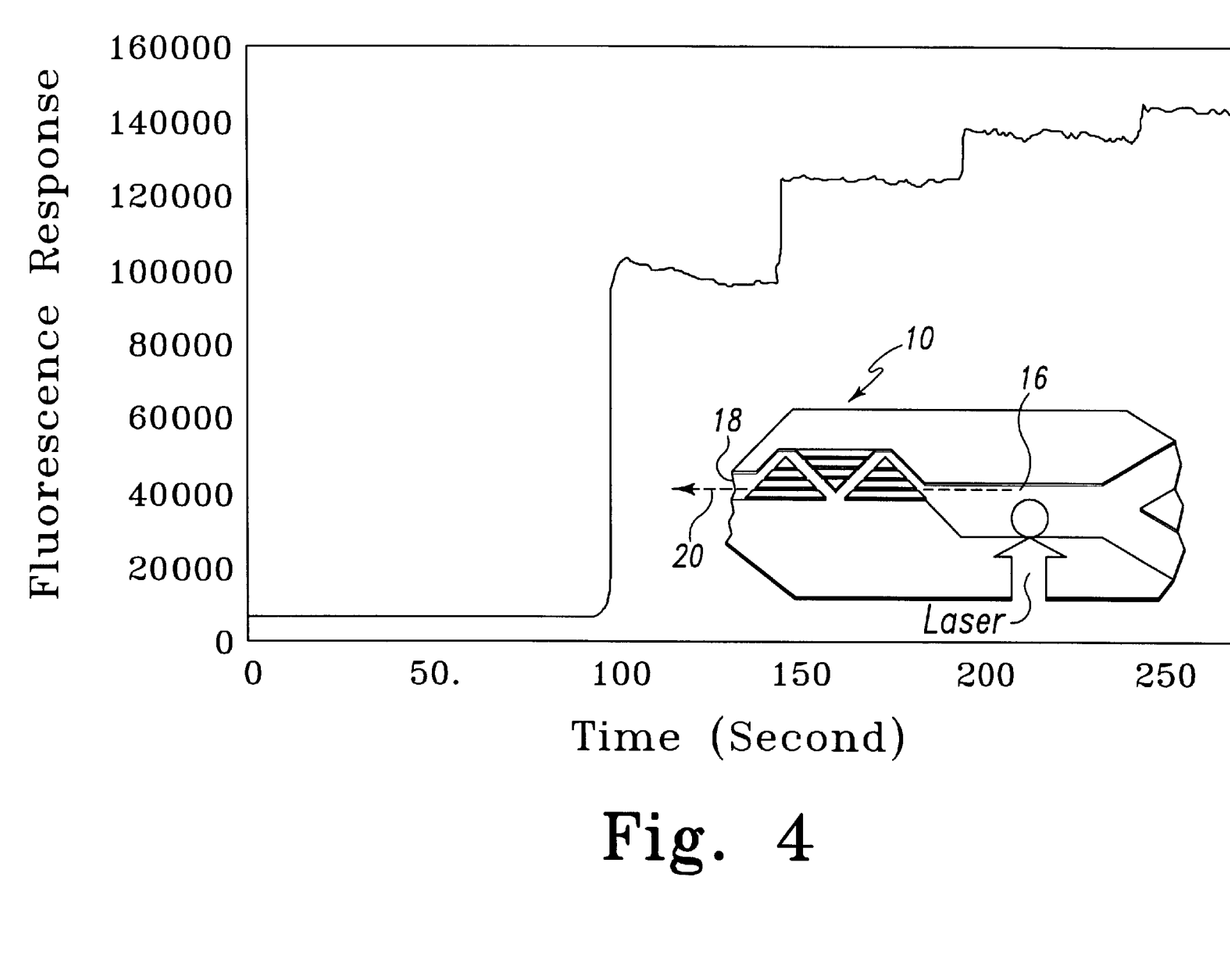
FIG. 4 is a graph of fluorescence response v. time, illustrating laser induced fluorescence monitoring of solvent composition at the inlet of the mixer of FIG. 1.

Assessment of mixing efficiency was next examined by laser induced fluorescence. The laser beam was positioned on the inlet 16 channel to the mixer, roughly 25 μm beyond the point of solvent contact, in such a way that only a portion of the channel was illuminated on the side next to the B solvent inlet, as shown in FIG. 4. This unusual configuration was chosen for two reasons. One is that there is lateral heterogeneity in solvent composition across the inlet 16 channel and spatial variations were expected as the solvent ratio changes. The second is that the laser beam is so wide it would cover most of the width of the channel if positioned in the middle of the inlet 16 channel and could not detect lateral differences in composition. Because manual alignment of the laser beam through the microscope is not very precise and it is difficult to define alignment coordinates, all the data presented below were collected without changing the alignment of the laser.

In the prior art, gradient formation has been reported in CEC based upon the application of voltage ramps to solvent reservoirs. It has been shown that this is a precise method of controlling solvent composition and developing gradients. Using the laser induced fluorescence detector described above, several important characteristics of the mixer 10 were noted from the measurements graphed in FIG. 4. One is that the detector responded rapidly to 100 msec changes in voltage at the solvent reservoirs. This is as expected, but is very different than at the outlet of the mixer 10 (100 μm away), as will be shown below. The second is that linear variations in voltage at the solvent reservoirs, which should have produced linear steps in the solvent composition, did not yield linear changes in fluorescence at the inlet to the mixer 10 roughly 50 μm beyond the point of solvent confluence. The interpretation of these results is that, in fact, there was a linear change in the solvent ratio entering the mixer 10 but that it was not seen by the detector because the laser beam was positioned asymmetrically toward the solvent B side of the inlet 16 channel. Although the solvent ratio entering the mixer was 80/20 (A/B), the solvent composition on the solvent B side of the mixer was roughly 40/60 (A/B) according to the data in FIG. 4. The non-linearity of response to linear increases in the amount of solvent B introduced into the mixer inlet 16 is interpreted to mean that the A and B solvent streams remain relatively segregated before they enter the mixer 10. Despite the low spatial precision of the measurement data caused by the width of the laser beam, the results of FIG. 4 still indicate very poor mixing in the inlet 16. These observations are consistent with those made by microscopy (FIG. 2A).

Figure 5:
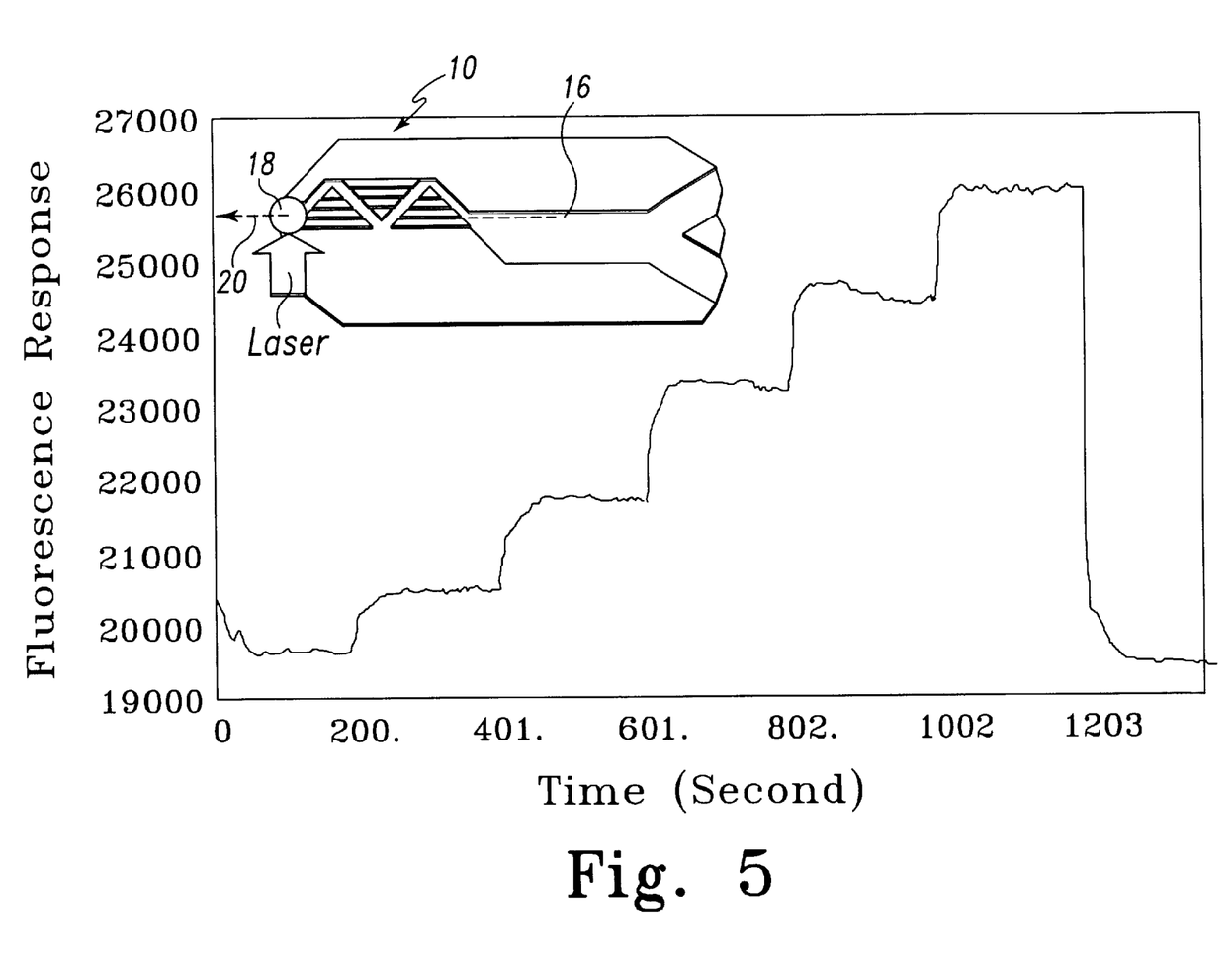
FIG. 5 is a graph of fluorescence response v. time, illustrating laser induced fluorescence monitoring of solvent composition at the outlet of the mixer of FIG. 1.

As illustrated in FIG. 5, data taken at the outlet 18 of the mixer 10 using the same detection strategy are very different. Note that the inlet 16 and the outlet 18 define an flow axis 20 therebetween. It is seen that there is a linear change in fluorescence with linear changes in solvent ratio introduced at the mixer 10 inlet 16. This is very different than at the inlet 16 of the mixer 10 and is interpreted to mean that mixing is complete at the mixer 10 outlet 18. Again, this is supported by the photomicrographs (FIG. 2B). The other major point to be noted is the much longer response time at the outlet 18 than the inlet 16 of the mixer 10. This observation is consistent with the conclusion that there is vortex mixing in the system. The presence of a vortex and perhaps counter flow would cause behavior similar to that of stirred tank mixers with concomitant longer response times. The microfabricated mixer 10 of the present invention appears to be very similar in mixing characteristics conventional mechanical mixers, except that it has no mechanical parts and is $10^5$–$10^7$ times smaller.

CONCLUSIONS

Rapid and complete mixing is a critical issue in microfluidic systems used for chemical reactions and chromatography. Based upon data presented herein, it is concluded that when two, or perhaps more, electroosmotically pumped liquid streams enter a microchannel of $\geq$50 μm width from spatially different points in a microfluidic system i) little mixing occurs within the first 100 μm of transport distance after contact and ii) the small amount of mixing that does occur is by diffusion alone. This has serious implications. In the case of rapid chemical reactions, substantial product would be produced at the interface of reactant streams before the reaction starts throughout the bulk of the solution. The consequences in eluting a liquid chromatography column with a mobile phase of lateral heterogeneity are equally serious. Band spreading would be increased by the higher rate of analyte migration on one side of the column.

The experimental results presented hereinabove lead to the conclusion that liquid streams can be efficiently mixed in a microfluidic system by passage through a complex of crossing channels located between collocated monolith support structures in a 50×200 μm mixer of roughly 100 pL volume. It is further concluded that creation of a vortex in the center of this device plays a role in mixing. Finally, it is concluded that mixers of this type should be of broad utility in all microfluidic systems where mixing is required.

MATERIALS AND METHODS USED IN THE PREFERRED EMBODIMENT

Materials. Photolithography masks, SL-4006-2C-AR3-AZ1350, and quartz wafers, QZ-3W40-225-UP, were purchased from HOYA Corp. (Shelton, Conn.). This quartz wafer, 3" in diameter and 400 μm thick, has an extremely low thermal expansion coefficient (<5×$10^{-7}$/K) and an ultra flat surface (>3 μm variation across the whole wafer surface). Both materials are shipped in sealed packages of 20. These packages should only be opened and handled under clean-room conditions.

Mask Fabrication. Filter chip layout was carried out on a SUN SPARK workstation (Sun Microsystem, Cupertino, Calif.) using IC-Station of Mentor Graphics (Wilsonville, Oreg.) at the Purdue University Solid State Laboratory. "Layout" files in the IC-Graphics format were then converted into GDS format, electronically transferred, and compiled to function as motion control files for the electron-beam drilling machine used in mask fabrication. The photomask, SL-4006-2C-AR3-AZ1350, of the designed filter well system was pattern generated using a variable aperture to the UV exposure region of the mask plate (UV beam, 365 nm). Due to the repetitive nature of the support monolith, the whole filter structure was generated on the mask by continuously stepping a 10X master of the unit cell until the whole filter was generated.

Microchip Fabrication. The filter well microchip was fabricated in Alberta Microelectronic Center (Edmonton, Alberta, Canada). The quartz wafers, QZ-3W40-225-UP, used in these studies were supplied coated with a 1 $\mu$m layer of Olin HPR504, a thick positive photoresist. After soft baking, exposure was carried out on a Karl Suss MA4 aligner. The wafers were then hard baked and the resist manually developed to preserve small structural features. Parallel plasma therm reactive ion etching using flourine based chemistry was used to dry-etch the wafers. This anisotropic etching process was used to produce the requisite high symmetry channels in the substrate of the primary wafer. Access holes were drilled on the cover wafer by stationary milling with a Sonic-Mill (Albuquerque, N. Mex.) fitted with a 1,000 $\mu$m bit. The centers of access holes drilled in the cover wafer were aligned to the center of the filter well in the etched wafer. Prior to wafer bonding, all wafers were thoroughly cleaned with ammonia and hydrogen peroxide to remove organic materials and particles. Wafer bonding was achieved by thermal fusion in a high temperature furnace. Pyrex glass tubing that had been cut into 8 mm segments (4 mm ID and 1 mm thickness) was bonded over the access holes on the cover wafer with epoxy adhesive to form buffer wells. Bonded wafers were stored in a dust free environment to prevent contamination of the access holes.

Chip Treatment. Internal surfaces of the chip were activated to produce the high density of silanol groups necessary for both wafer surface wetting and electroosmotic pumping. All buffer wells were filled with a mixture of $MeOH:H_2O$ (1:1) with one outlet connected to a Barnant (Barrington, Ill.) vacuum pump. A 20 mmHG vacuum was applied to wet the internal surface of the microchip. 0.1 M NaOH was then introduced and retained for 1 hour to activate the silanol groups on the internal surface. The microchip was then rinsed with $MeOH:H_2O$ (1:1). Finally, the column was treated with 10 mM, pH 7.0 potassium phosphate buffer.

Microfluidic Voltage Control. Sample loading and separations were achieved by a computer controlled power supply. A National Instruments (Austin, Tex.) AT-AO-10 analog power output card was used to generate an analog voltage signal (0–10 Volts, 0–20 mA) for up to 10 channels. This analog voltage was then amplified 1,000 fold using Gamma (Ormond Beach, Fla.) PMT10-0.1P/M power supplies to provide voltage output of 0–10,000 volts and current output up to 100 $\mu$A for each channel. These PMT10-0.1P/M power supplies amplified the voltage output in a regulated pattern, so precise output is expected. The AT-AO-10 card was protected by the parallel installed Digikey (Thief River Falls, Minn.) transorb diodes on the PMT10-0.1P/M power supply to prevent possible back currents from the power supplies. Voltage Output, for up to 10 channels, are programmable through a voltage control program developed by VI Engineering (Indianapolis, Ind.).

Laser Induced Fluorescence Detection. All separations were monitored by a laser induced fluorescence detection system. An air cooled Uniphase (San Jose, Calif.) 2011-10SL argon-ion laser with a 10 mW output at 488 nm was used as the laser excitation source. A Newport (Irvine, Calif.) DM5 argon ion high reflector was used to direct the laser beam. DM5 has a high reflectance efficiency, $R_sR_p>99\%$ when used for laser beams of 488–514 nm in 0–45°. A long working distance MELLES GRIOT achromatic microscope objective (10×, WD 6.8 mm, F16.9 mm) was used to focus the laser beams on the detection points in the microchip while providing sufficient space for peripheral apparatus around the chip and positioning monitors. The microchip was positioned using a homemade holding device. The design of the holding device provides sufficient space around the microchip, which is necessary not only for the installation of the peripheral devices, but spatial clearance for high voltage operation on the microchip. The holding device is connected to a Newport 460 XYZ positioner which provides submicron positioning precision for easy focusing of the laser beam. Another MELLES GRIOT achromatic microscope objective with relatively short working distance (16×, WD 3.7 mm, F10.8) was used to maximize collection of the emitted fluorescence from its emitting sphere. Two optical filters were used to eliminate the unwanted scattered laser beams: The Schott band pass filter (OG 515) and the HSNF-488-1.5 Kaiser super holographic notch filter. The OG-515 filter effectively reduces any light passage with a wavelength lower than 490 nm, while HSNF-488-1.5 selectively reduced the transmission at 488+5 nm. A R928 side-on Hamamatsu photomultiplier was used to collect the fluorescence. The high sensitivity (250 $\mu$m/Im), broad spectral response from the ultraviolet to near infrared region (185–930 nm, 400 nm peak) with high quantum efficiency (5–10% in visible region), low dark current (3.0 nA after 30 mins), and reasonably maximum linear current (0.1 mA) makes it very suitable for this application. A Keithley 485 autorange picoammeter was used to collect the current signal from the Hamamatsu R928 photomultiplier. The Keithley 485 autorange picoammeter features a broad measurement range from 2 nA to 2 mA, which suits well the normal output of the Hamamatsu R928 photomultiplier tube. A National Instrument AT-GPIB/TNT (Plug and Play ISA) board was used to interface the picoammeter and the microcomputer for data acquisition and storage. Fluoresein solution ($10^{-4}$ M) in sodium phosphate buffer (10 mM, pH 9, with trace of methanol) was used to monitor the laser induced fluorescence signal.

Confocal Fluorescence Photomicrography. A Nikon Inverted Eclipse TE-300 optical microscope, equipped with a TE-FM epi-fluorescence attachment, was used to monitor the performance of the mixer. Fluorophore solution used here is the same as the one used in laser induced fluorescence detection experiment, $10^{-4}$ M in sodium phosphate buffer (10 mM, pH 9, with trace of methanol). A Nikon EF-4 B-2E/C FITC filter cube was used with fluoresein because of their similar excitation and emission characteristics. This filter cube selectively allows the passage of lines around 488 nm as the excitation beam, but blocks them from entering the detection window. A Sony DXC-151A color CCD camera was used on the side port to collect real time fluorescence images. A SVO-2100 VCR was used to record the video images, and the process was monitored by a Sony PVM-1353MD monitor.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A microfluidic mixer, comprising:
   an inlet;
   an outlet, wherein the inlet and the outlet define a flow axis extending therebetween;
   a first flow channel extending between the inlet and the outlet, wherein the first flow channel includes a first section oriented at an obtuse angle to the flow axis and a second section oriented at an acute angle to the flow axis, thereby defining a substantially triangular region bounded on two sides by the first and second sections;

a plurality of second flow channels disposed in the substantially triangular region, each of said second flow channels allowing fluid flow between the first and second sections substantially parallel to the flow axis.

2. The microfluidic mixer of claim 1, wherein the first flow channel has a substantially larger cross-sectional area than each of the second flow channels.

3. The microfluidic mixer of claim 2, wherein the first flow channel cross-sectional area is approximately five times larger than each of the second flow channel cross-sectional areas.

4. The microfluidic mixer of claim 1, wherein the first section is oriented at a substantially 135° angle to the flow axis, and the second section is oriented at a substantially 45° angle to the flow axis.

5. The microfluidic mixer of claim 1, wherein each of the plurality of second flow channels are of a different length.

6. The microfluidic mixer of claim 1, wherein the first flow channel and each of the second flow channels are formed in a quartz substrate.

* * * * *

UNITED STATES PATENT AND TRADEMARK OFFICE
CERTIFICATE OF CORRECTION

PATENT NO.   : 6,170,981 B1
DATED        : January 9, 2001
INVENTOR(S)  : Regnier et al.

It is certified that error appears in the above-identified patent and that said Letters Patent is hereby corrected as shown below:

Column 4,
Line 45, please change "≤" to -- $\leq$ --.
Line 62, please change "≥" to -- $\geq$ --.

Column 6,
Line 22, please change "≥" to -- $\geq$ --.

Column 8,
Line 19, please change "488+5" to -- 488±5 --.

Signed and Sealed this

Thirtieth Day of July, 2002

Attest:

JAMES E. ROGAN
Attesting Officer     Director of the United States Patent and Trademark Office